US007862227B2

(12) United States Patent
West et al.

(10) Patent No.: US 7,862,227 B2
(45) Date of Patent: Jan. 4, 2011

(54) METHOD AND APPARATUS FOR TESTING BUILDING MATERIALS

(75) Inventors: Richard A. West, 3103 Nantucket Row, Bay Village, OH (US) 44140; Michael R. Rosecrans, Sullivan, OH (US)

(73) Assignee: Richard A. West, Bay Village, OH (US)

( * ) Notice: Subject to any disclaimer, the term of this patent is extended or adjusted under 35 U.S.C. 154(b) by 292 days.

(21) Appl. No.: 12/058,159

(22) Filed: Mar. 28, 2008

(65) Prior Publication Data

US 2008/0267252 A1    Oct. 30, 2008

Related U.S. Application Data

(60) Provisional application No. 60/920,470, filed on Mar. 28, 2007.

(51) Int. Cl.
 *G01N 25/00* (2006.01)
(52) U.S. Cl. .............................. 374/8; 374/31; 374/38; 374/45
(58) Field of Classification Search ...................... 374/8, 374/31, 38, 45
See application file for complete search history.

(56) References Cited

U.S. PATENT DOCUMENTS 3,930,397 A * 1/1976 Suga ............................. 374/8
3,987,661 A * 10/1976 Kamp et al. .................... 374/8
4,637,735 A * 1/1987 de Ris et al. .................... 374/8
6,336,943 B1 * 1/2002 Login et al. .................... 8/195
2009/0168833 A1 * 7/2009 Sarabi et al. .................... 374/8

* cited by examiner

*Primary Examiner*—Lisa M Caputo
*Assistant Examiner*—Mirellys Jagan
(74) *Attorney, Agent, or Firm*—Fay Sharpe LLP

(57) ABSTRACT

An apparatus (A) for testing an associated construction material sample includes a housing (20) having an internal chamber (22) divided by a wall portion (30) into first and second portions (24, 26). A support in the housing is dimensioned to mount an associated construction material sample therein. A first burner (60) communicates with first portion of the housing for supplying a flame thereto. A second burner (80) communicates with the second portion of the housing for preheating the first portion. The testing method of an associated construction material sample includes installing the sample in the housing, preheating the housing, introducing a flame toward the sample, monitoring the flame as combustion progresses longitudinally along the sample, and recording data regarding the flame progression. The method further includes weighing fuel used for combustion in order to calculate BTU input to the test chamber, may also include using a remote (98) to actuate a recording member (94) that is selectively advanced as the flame spreads, and may further include providing a continuous window along the housing through which the flame can be viewed.

21 Claims, 4 Drawing Sheets

METHOD AND APPARATUS FOR TESTING BUILDING MATERIALS

This application claims the priority benefit of, and expressly incorporates the entire disclosure of U.S. provisional application Ser. No. 60/920,470, filed Mar. 28, 2007.

BACKGROUND OF THE INVENTION

This application relates to a testing apparatus, and more particularly to an apparatus for flame testing of materials such as building materials. It finds particular application in testing polyurethane roofing or insulation, but should not be limited to these particular building materials. Thus, the method and apparatus may find use with regard to related materials and testing.

It is common to expose building materials to combustion, and particularly test a sample under controlled procedures in order to determine the relative burning behavior as typically measured by the spread of the combustion flame, as well as measuring smoke that is developed during the test. For example, ASTM Standard E 84-06 entitled "Standard Test Method for Surface Burning Characteristics of Building Materials" discloses a fire test chamber that is a rectangular cross-section, horizontal tunnel or duct having multiple windows spaced longitudinally along the tunnel length. A building material sample is received in the test chamber or duct such that a first end is disposed adjacent a gas burner that delivers combustion flames against the surface of the test sample. A predetermined gas flow and regulated pressure delivers the combustion fuel and, in addition, induced airflow is provided to advance the flame along the sample. An exhaust fan is provided at the opposite end of the test apparatus to create the desired airflow.

In addition, a photometer or lamp photocell is mounted in the chamber to indicate the amount of smoke generated during the test. Similarly, one or more thermocouples are provided in the test chambers to record the temperature. The test apparatus is calibrated relative to red oak and/or fiber cement board test samples. Particularly, the flame spread distance, temperature, and change in the photoelectric cell readings as a result of testing these materials are used to assign values for a tested sample relative to these baseline values. For example, a flame spread index (FSI) is calculated on the progression of the flame over a longitudinal distance and in a certain amount of time.

In a similar manner, Underwriters' Laboratories, Inc. (UL) has its own standard test methods for fire tests for various building materials. For example, one such fire test for roof coverings is UL790 Standard. By way of example, the UL standard requires the test sample to be forty (40) inches wide by eight (8) feet long. The sample is prepared to a desired thickness. The sample must be cured for twenty-eight (28) days. A slope is provided in the test apparatus and the sample is mounted therein. The sample is then burned for ten (10) minutes with specified temperatures and wind speeds. By way of example only, a test limit for spread of flame is six (6) feet in length with no burn-off of the lateral edge. The test results are then tabulated and reported to the building materials manufacturer.

Substantially all building material manufacturers submit samples to either UL or Factory Mutual in order to determine the flammability (spread of flame) and how much smoke is generated by the material. A Steiner tunnel test requires a sample that is twenty-four (24) feet long, and two (2) feet wide to be submitted for these types of tests. As noted above, a flame is introduced at one end, a draft created at the other end, and the flame is observed as it moves toward the exhaust end over a ten (10) minute test, for example. A photometer determines the density of the smoke so that a smoke density ratio is also provided.

If the manufacturer finds the sample does not achieve the desired ratings as a result of conducting these tests, the manufacturer is relegated to creating new samples for submission and undertaking additional tests. This procedure can become cost prohibitive, For example, development of a new building material may result in a large number of tests as the manufacturer "tweaks" the formulation of the product. Each test costs approximately fifteen-hundred dollars ($1,500). Creating the sample and shipping the samples to the test laboratories may cost between three and five thousand dollars ($3,000-$5,000) per sample, and even then there is a three to four week delay in order to have the test completed. As will be appreciated, when hundreds of tests are undertaken, the cost, timing, etc. requires the manufacturer to limit the amount of research and development in creating new formulations, and/or be judicious with regard to the number of samples submitted for testing.

Thus, a need exists for a preliminary test that can be conducted on dimensionally scaled-down samples, at substantially reduced costs, and in a substantially reduced time frame.

SUMMARY OF THE INVENTION

An apparatus for testing an associated construction material sample includes a housing having an internal chamber divided by a wall portion into first and second portions. A support in the housing is dimensioned to mount an associated construction material sample therein. A first burner communicates with first portion of the housing for supplying a flame thereto. A second burner communicates with the second portion of the housing for preheating the first portion.

First and second exhaust openings communicate with the first and second portions, respectively.

Means for measuring the weight of fuel consumed by the first burner is also provided.

A recorder member is provided to indicate the longitudinal flame spread through the first portion of the housing.

A remote control member is operatively connected to the recorder member to record location of the flame spread.

A data storage receives information from the recorder member for storing information related to the test such as rate and distance of flame spread, temperature, BTUs, smoke generation, etc.

A continuously extending window is provided along a substantial length of the housing for viewing the longitudinal spread of the flame.

Means for adjusting the position of the construction material sample may also be provided.

A method of testing an associated construction material sample includes installing the sample in the housing, preheating the housing, introducing a flame toward the sample, monitoring the flame as combustion progresses longitudinally along the sample, and recording data regarding the flame progression.

The method further includes weighing fuel used for combustion in order to calculate BTU input to the test chamber.

The method may also include using a remote to record a longitudinal progression of the flame.

The method may further include providing a continuous window along the housing through which the flame can be viewed.

A primary advantage of the invention resides in the ability to pre-test samples of construction materials before submission to a testing laboratory.

Another advantage offered by the present disclosure is the reduced cost.

Another advantage of the invention resides in the improved turn-around time to conduct the tests.

Still another advantage resides in the ease with which the testing may be undertaken, along with the ability to preheat the test chamber, weigh the combustion fuel used, and measure the flame progression during the test.

Still other advantages and benefits of the present disclosure will become apparent to one skilled in the art upon reading and understanding the following detailed description.

DETAILED DESCRIPTION OF THE DISCLOSURE

Figure 1:
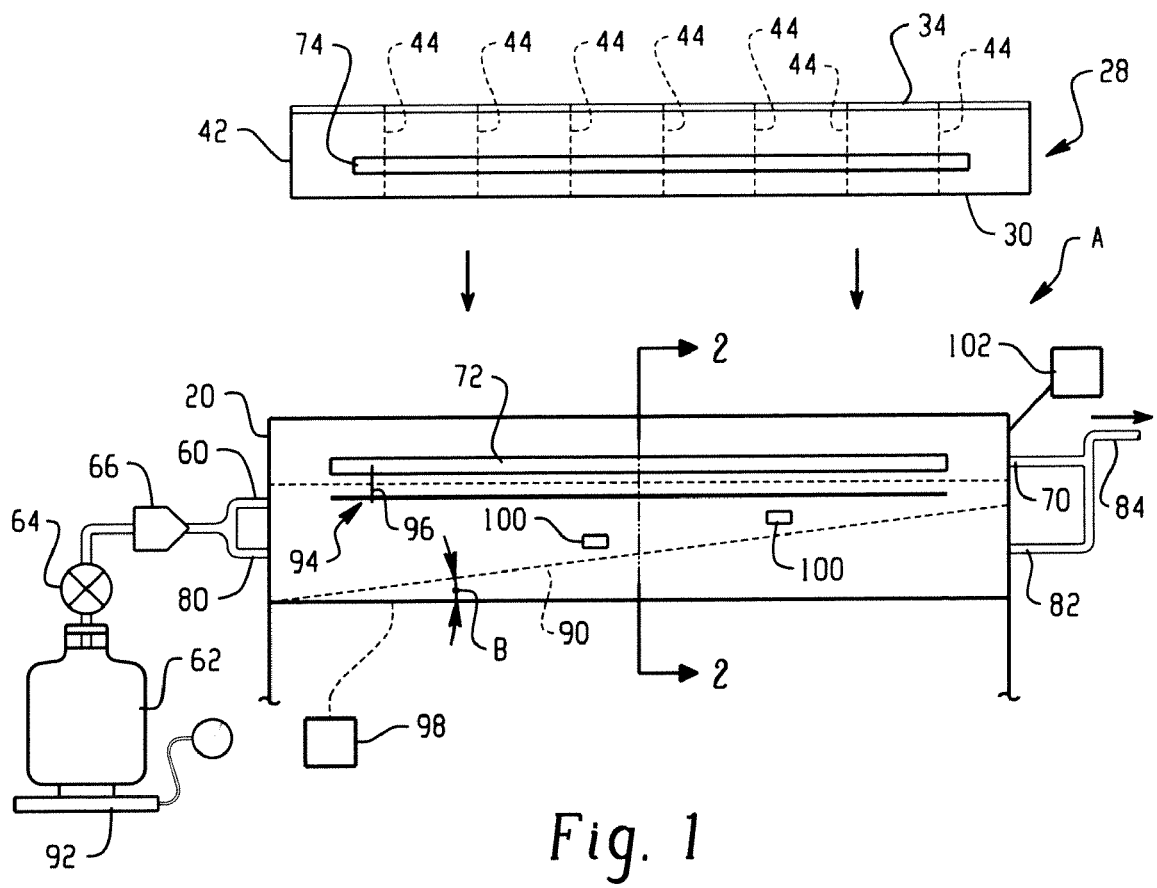
FIG. 1 is a schematic illustration of the test apparatus with an insert shown separated from the remainder of the apparatus for installation therein.

FIG. 1 shows a test apparatus A that includes a housing 20 that has an internal chamber 22. The internal chamber is preferably divided into first and second portions 24, 26 by an insert 28 that includes a wall 30 that extends along a longitudinal extent of the chamber when the insert is received in the housing. Particularly, flanges 32, 34 of the insert are supported on shoulders 36, 38 in the housing. The flanges extend outwardly from sidewalls 40, 42 of the insert. Further, baffles 44 may be provided in the insert, and preferably extend inwardly from the sidewalls 40, 42 at longitudinally spaced locations along the length of the insert.

Figure 2:
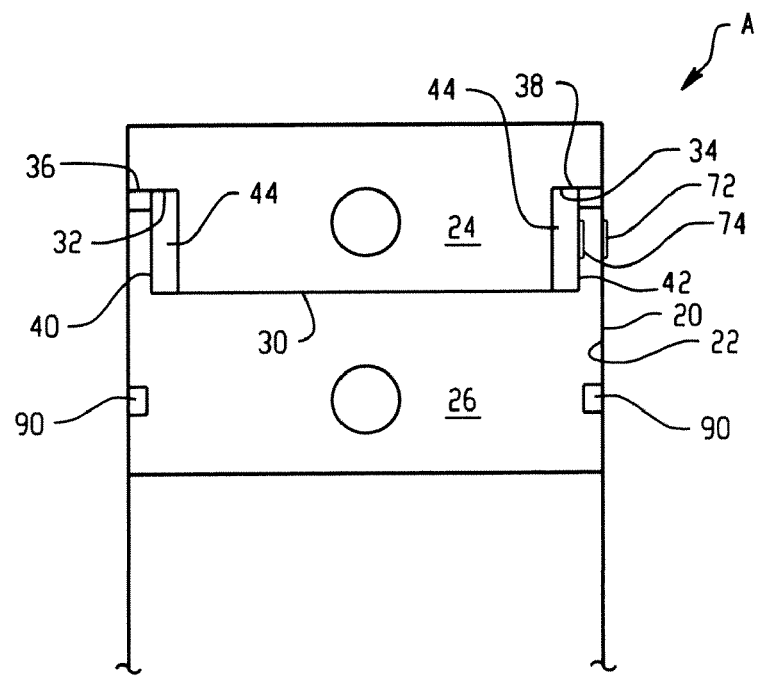
FIG. 2 is a cross-sectional view taken generally along the lines 2-2 of FIG. 1.

As best illustrated in FIG. 2, when the insert is mounted in the housing 20, bottom wall 30 defines the chamber 22 into the first and second portions 24, 26. With reference again to FIG. 1, a first or upper inlet 60 is disposed at one end of the upper or chamber first portion 24. The first inlet communicates with a combustion fuel source such as a propane tank 62, natural gas source, or another accepted fuel source. Shut-off valve 64 and regulator 66 control the supply of the fuel to the first inlet, and particularly supply the fuel in accordance with scaled down parameters that allow the test apparatus to be effectively used to simulate tests that would be administered to building material samples by independent laboratories.

A first or upper exhaust opening 70 is provided at the opposite axial end of the chamber first portion 24. In this manner, a test sample (not shown) received in the chamber will be burned or combusted from the first end in a manner so that the flame propagates or longitudinally spreads toward the exhaust opening 70. In order to monitor the flame spread, a window 72 is provided in the housing. The window is preferably continuous along its longitudinal length and extends over substantially the entire longitudinal extent of the chamber. This is to be contrasted with prior art arrangements where segmented window portions are provided along the length of the test chamber. Likewise, a similar window 74 is matingly aligned in the insert sidewall 42 so that when the insert is received in the housing, the flame can be viewed through the aligned windows 72, 74 from a location external to the housing.

A second inlet 80 also communicates with the inlet (left-hand end in FIG. 1) of the housing chamber. At the opposite end is disposed a second outlet or exhaust opening 82. Both the inlet 80 and the exhaust opening 82 are advantageously used to preheat the chamber first portion 24 by separately heating the chamber second portion 26. That is, the chamber second portion extends along the length of the housing chamber and the temperature of the wall 30 and the sidewalls 40, 42 of the insert, and thus the temperature of the chamber first portion 24, can be quickly brought up to a desired level by heating the chamber second portion 26. As illustrated in FIG. 1, the first and second inlets 60, 80 are connected externally of the test housing, and likewise the first and second exhausts openings 70, 82, are connected externally of the housing. In this manner, the same fuel source 62 is used to supply both the chamber first and second portions 24, 26 and combustion gases can be effectively removed at the opposite ends by the respective exhaust openings 70, 82 which combustion byproducts are removed from the test site through passage 84.

Also provided in the housing is a second support 90, for example, provided by first and second shoulders (FIG. 2) that extend inwardly into the chamber from respective sidewalls of the housing 20. The second support is preferably disposed at an angle that increases relative to the bottom of the housing as it proceeds from the inlet toward the exhaust (FIG. 1). The second support may be fixed relative to the housing, or preferably is adjustable so that the angle B may be altered. It will be appreciated that the ability to use an angled support, such as for roofing or ceiling material testing, or a fixed or horizontal support, such as used to test building insulation, allows a single test apparatus A to be used for different types of tests.

Also shown in FIG. 1 is an alternative manner of monitoring the BTUs added to the test apparatus. More particularly, the energy input into the test apparatus is calculated by measuring the weight of the combustion fuel used. By way of example only, it is known how many BTUs are associated with a pound of propane. It is also known that the standard test is ten minutes long. Therefore, by measuring the amount of propane used by weighing or monitoring the weight of the fuel source on scale 92, an accurate measurement of the BTUs input into the test apparatus can be calculated.

Propagation of the flame is measured by recording member 94. Particularly, the recording member is movable along the length of the housing and preferably has a pointer or other indicia 96 disposed adjacent the window 74. The recording member is actuated for movement in the longitudinal direction, for example by rotating a threaded rod such that a follower (that serves as the pointer on the threaded rod) is axially advanced along the rod. The longitudinal position of the flame can be marked or identified. By providing a remote control 98, test personnel viewing the flame propagation through the window from a location adjacent the housing actuate the recording member to travel from the inlet toward the outlet in the same manner as the flame advances along the test sample. Since the window is continuous along its length, as the flame advances, the test personnel merely advances the pointer of the recording member as the flame spreads toward the exhaust end of the housing chamber.

In addition, a preferred arrangement incorporates at least one, and preferably two, temperature probes 100 into the building material sample. The particular location within the sample may be varied. This provides a unique feedback from the sample during the flame test. Data from the temperature probe(s) are used to provide further information to the manufacturer which, of course, can be advantageously used in development of the building material. The temperature probes are shown in FIG. 1 at representative locations in the test chamber, although it with be understood that preferably the probes are placed directly in the sample, or at a different location depending on the type of test and location of the sample.

Data recorder 102 is operatively associated with the recording member and remote control. This allows information regarding the time and the longitudinal extent of the flame propagation toward the outlet to be recorded and stored in the data memory. Still other data from the test apparatus is input to the data recorder, for example, the temperature, smoke generation, BTUs, temperature(s) from the probe(s) in the sample, etc.

Figure 3:
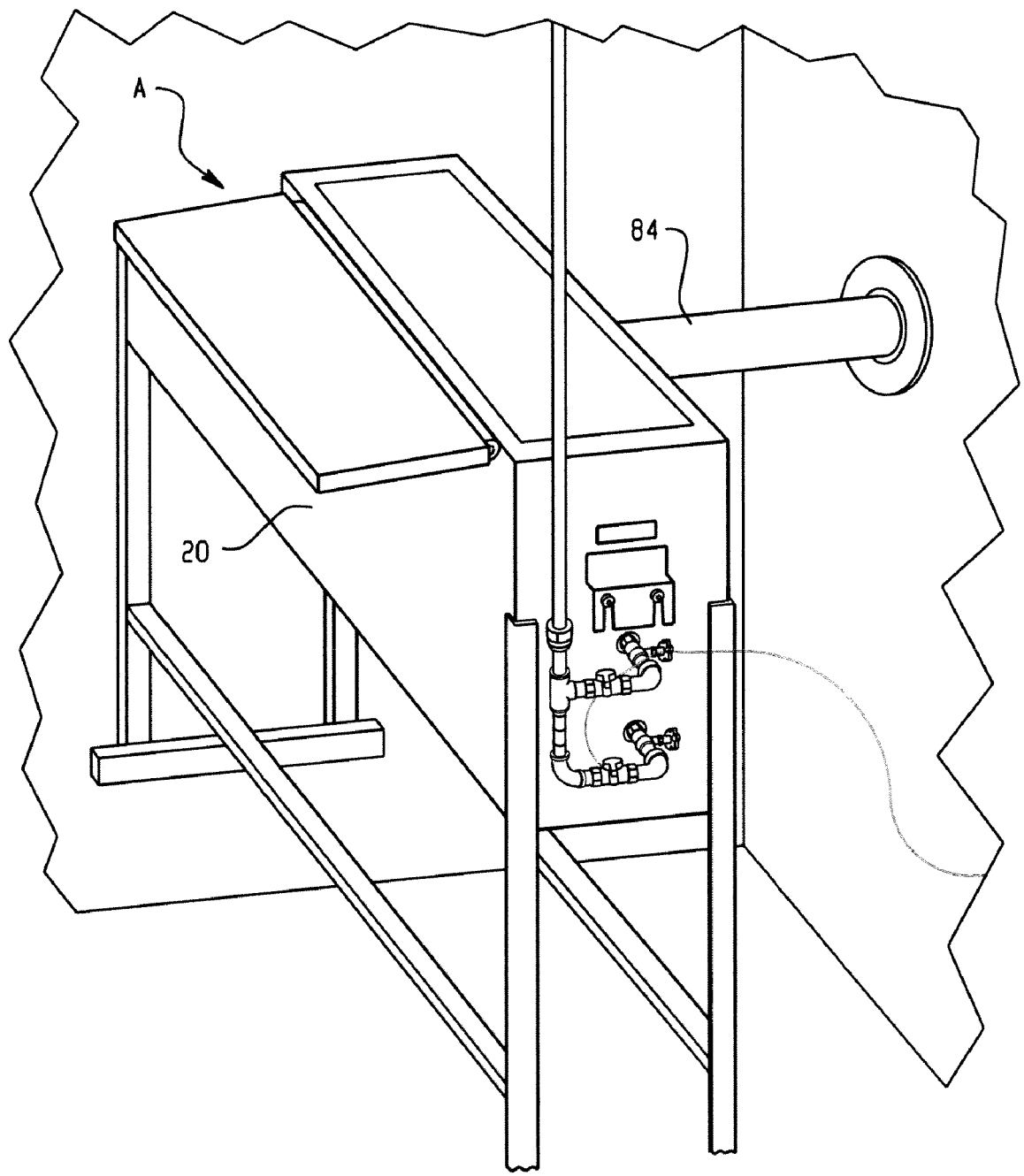
FIG. 3 is a perspective view of a test apparatus.
Figure 4:
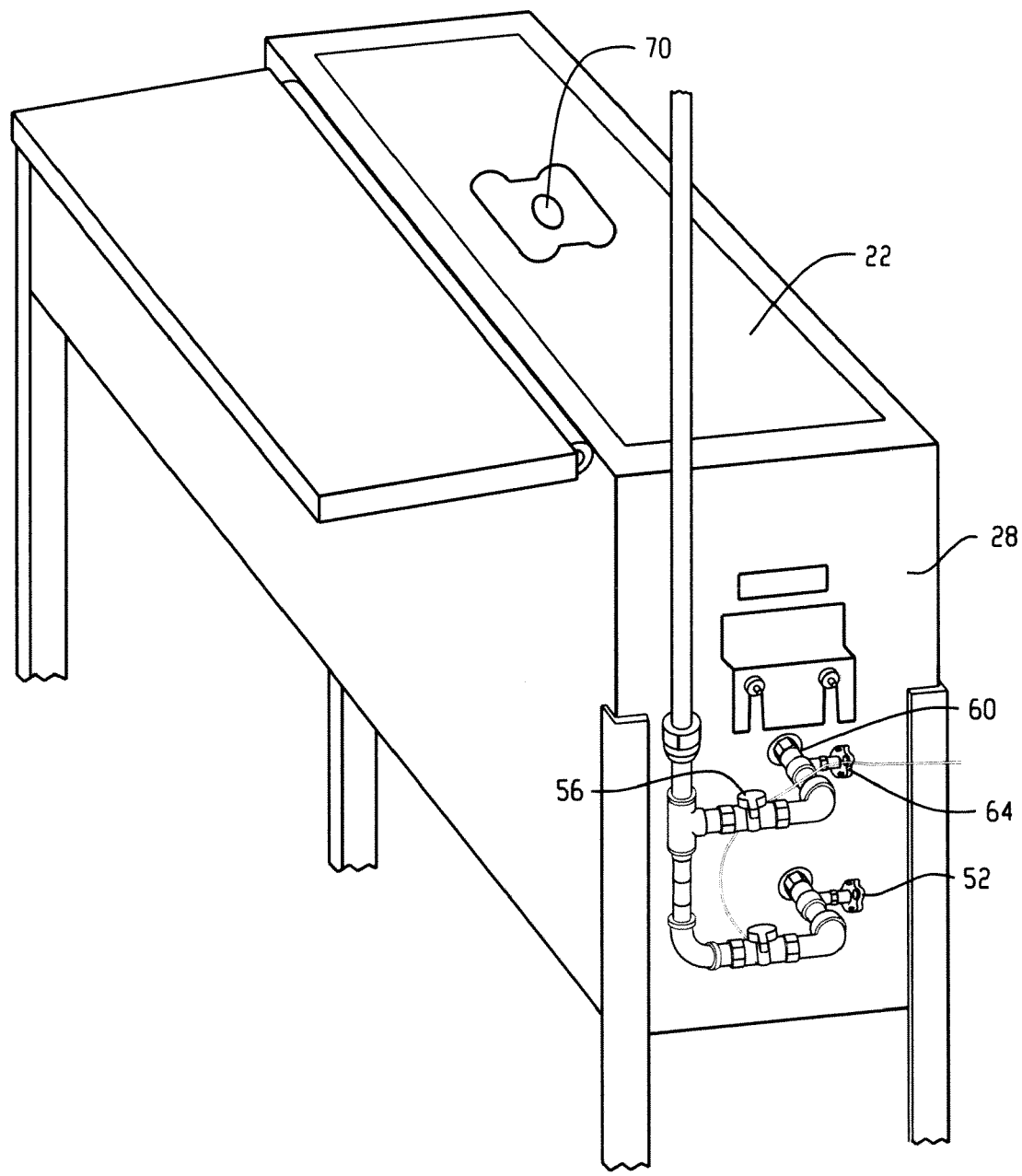
FIG. 4 is an end view of the inlet end of the test apparatus of FIG. 3.
Figure 5:
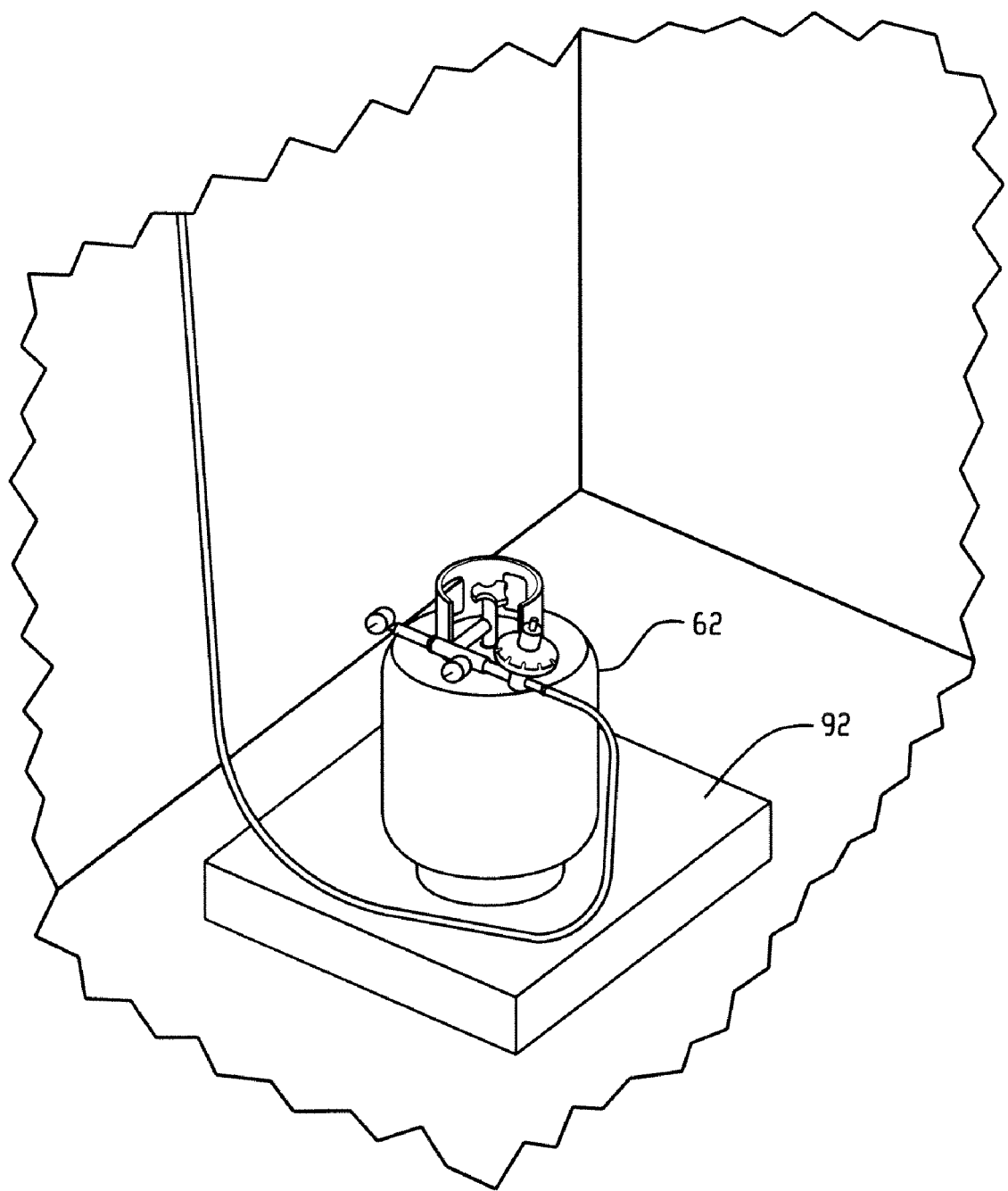
FIG. 5 is a fuel source received on a scale for supplying combustible fuel to the apparatus of FIGS. 1-4.

FIGS. 3-5 are images of a prototype test apparatus. The inlet end is shown in FIGS. 3 and 4, where the first and second inlets are shown to be commonly supplied. Both regulator and shutoff valves are provided for each inlet. FIG. 5 shows the combustible fuel source. Again, the pressure is regulated, and the amount of fuel used is monitored by the scale.

The particular locations of the inlets 60, 80, and likewise the exhaust openings 70, 82 are dictated by the testing procedures. In accordance with this arrangement, however, the housing has an internal dimension of approximately six (6) feet long and will accommodate a test sample approximately six (6) inches wide. This is substantially smaller than typical samples. That is, the test apparatus and samples are preferably one-fourth (¼) scale of those used in a typical Steiner tunnel test. This allows a building material manufacturer to purchase its own pre-test apparatus, so that the manufacturer would have a smaller test apparatus that would provide dependable, reproducible, and comparable test results to those that would be expected at the typical testing laboratory. Time to manufacture, the size of the sample, and the number of man hours involved with preparation of the test samples would all be significantly reduced, along with a substantial reduction in cost.

Moreover, the test apparatus is able to advantageously conduct two types of tests, i.e., any type of test that can be conducted in a Steiner tunnel and a test according to ASTM standards. For example, testing can occur for building material in the chamber first portion by mounting the insert in the housing and introducing a flame through the first burner inlet. Alternatively, the insert can be removed and a test sample mounted on the second support where, for example, flame testing can be conducted on a roofing material sample. Further, incorporating a lower chamber that can preheat the first chamber portion is also desirable, as well as the ability to measure BTU input by weighing the combustible fuel used. Smoke development is still determined in the same conventional way, that is, by using a light sensor or photometer incorporated into the test apparatus. Likewise, the temperature of the test chamber can be monitored and all of this data fed to the data storage 102. Greater accuracy regarding flame spread can also be achieved with the continuous window and remote control arrangement of the present disclosure. Further, the support can be adjustable to provide greater flexibility in testing procedures.

Ultimately, the test apparatus is not necessarily intended to replace the UL testing operation. Rather, the test apparatus provides significant cost savings to the manufacturer and greater flexibility in developing new formulations so that the manufacturer knows in advance with greater certainty the prospects for the material passing the test standards. A manufacturer will be able to test a number of products in advance, and with increased assurance that the product will be able to pass the flammability and smoke generation tests conducted by an outside testing facility.

The invention has been described with reference to the preferred embodiment. Obviously, modifications and alterations will occur to others upon reading and understanding the preceding detailed description. It is intended that the invention be construed as including all such modifications and alterations.

Having thus described the invention, it is now claimed:

1. An apparatus for testing an associated sample of construction material comprising:
    a housing having an internal cavity divided by a wall portion into first and second portions;
    a support in the housing for mounting an associated construction material sample in at least one of the first portion and the second portion;
    a first burner communicating with the first portion for supplying a flame thereto;
    a second burner communicating with the second portion for preheating the first portion; and
    a scale that measures a weight of fuel consumed by at least one of the first burner and the second burner.

2. The apparatus of claim 1 further comprising first and second exhausts communicating with the first and second portions, respectively.

3. The apparatus of claim 1 wherein the support is adjustable for positioning the associated construction material sample in different manners in the housing.

4. The apparatus of claim 1 wherein the housing is dimensioned to receive the associated construction material sample between the burners and an exhaust.

5. The apparatus of claim 1 wherein the housing includes a support flange for engaging at least a portion of a perimeter of the associated construction material sample.

6. The apparatus of claim 1 wherein the housing first portion has an internal dimension just slightly greater than 6 feet long and 6 inches wide.

7. The apparatus of claim 1 further comprising a light sensor for monitoring smoke development in the housing.

8. The apparatus of claim 1 wherein the first portion is defined at least in part by an insert received in and subdividing the housing.

9. The apparatus of claim 1 further comprising means for moving air through the housing.

10. The apparatus of claim 1 further comprising a recorder member that is indicative of a longitudinal flame spread through the first portion.

11. The apparatus of claim 10 wherein the recorder member is operatively connected to a remote control member for selective advancement of the recorder member in response to actuation of the remote control member.

12. The apparatus of claim 10 wherein the recorder member operatively communicates with a data storage for storing information relating to rate and distance of flame spread.

13. The apparatus of claim 10 further comprising a window extending continuously along a substantial length of the housing for viewing a longitudinal position of the flame on the associated construction material sample.

14. An apparatus for testing an associated sample of construction material comprising:
    a housing having an internal cavity divided by a wall portion into first and second portions;
    a support in the housing for mounting an associated construction material sample in at least one of the first portion and the second portion;

a first burner located adjacent a first end of the cavity communicating with the first portion for supplying a flame thereto;

an exhaust opening adjacent a second end of the cavity so that the flame propagates from the first end toward the second end; and a recorder member that measures flame as the flame spreads through the cavity from the first end to the second end.

15. The apparatus of claim 14 wherein the recorder member operatively communicates with a data storage for storing information relating to rate and distance of flame spread.

16. The apparatus of claim 14 further comprising a window extending continuously along a substantial length of the housing for viewing a longitudinal position of the flame on the associated construction material sample.

17. The apparatus of claim 14 wherein the recorder member is operatively connected to a remote control member for selective advancement of the recorder member in response to actuation of the remote control member.

18. The apparatus of claim 14 further comprising means for measuring weight of fuel consumed by at least one of the first burner and the second burner.

19. The apparatus of claim 14 further comprising first and second exhausts communicating with the first and second portions, respectively.

20. The apparatus of claim 14 further comprising a second burner communicating with the second portion for preheating the first portion.

21. The apparatus of claim 1 further comprising a second burner communicating with the second portion for preheating the first portion.

* * * * *